(12) United States Patent
Van De Heijning et al.

(10) Patent No.: US 8,637,487 B2
(45) Date of Patent: Jan. 28, 2014

(54) NUTRITIONAL PRODUCTS COMPRISING SACCHARIDE OLIGOMERS

(75) Inventors: Hubertus Josephus Maria Van De Heijning, Utrecht (NL); Houkje Bouritius, Zeist (NL); Katrien Maria Jozefa Van Laere, Heteren (NL); Robert Johan Joseph Hageman, Wageningen (NL)

(73) Assignee: N. V. Nutricia, Zoetermeer (NL)

( * ) Notice: Subject to any disclaimer, the term of this patent is extended or adjusted under 35 U.S.C. 154(b) by 605 days.

(21) Appl. No.: 12/513,330

(22) PCT Filed: Nov. 2, 2007

(86) PCT No.: PCT/NL2007/050530
§ 371 (c)(1),
(2), (4) Date: Oct. 8, 2009

(87) PCT Pub. No.: WO2008/054211
PCT Pub. Date: May 8, 2008

(65) Prior Publication Data
US 2010/0069327 A1    Mar. 18, 2010

(30) Foreign Application Priority Data
Nov. 2, 2006    (WO) ................ PCT/NL2006/050275

(51) Int. Cl.
*A61K 31/715*    (2006.01)
*A01N 43/04*    (2006.01)

(52) U.S. Cl.
USPC ............................................. 514/54; 514/53

(58) Field of Classification Search
USPC .................................................... 514/54, 53
See application file for complete search history.

(56) References Cited

U.S. PATENT DOCUMENTS

| 6,946,451 B2 | 9/2005 | Takada et al. |
| 7,091,194 B1 | 8/2006 | Jann et al. |
| 7,422,763 B2 | 9/2008 | Wolf et al. |
| 7,618,951 B2 | 11/2009 | Monsan et al. |
| 8,053,471 B2 * | 11/2011 | Stahl et al. ..................... 514/546 |
| 2008/0124323 A1 * | 5/2008 | Boehm et al. .............. 424/132.1 |

FOREIGN PATENT DOCUMENTS

| EP | 0 898 900 B1 | 10/2003 |
| EP | 1 060 673 B1 | 7/2004 |
| EP | 1588629 A1 * | 10/2005 |
| EP | 1 629 850 B1 | 5/2007 |
| EP | 1 588 629 B1 | 5/2009 |
| JP | 2002-306131 A | 10/2002 |
| JP | 2003-516757 A | 5/2003 |
| JP | 2003-292444 A | 10/2003 |
| JP | 2004-149471 A | 5/2004 |
| WO | WO-01/44489 A2 | 6/2001 |
| WO | WO-01/67895 A1 | 9/2001 |
| WO | WO-2004/024167 A2 | 3/2004 |
| WO | WO-2005/039319 A2 | 5/2005 |
| WO | WO-2006/009437 A2 | 1/2006 |

OTHER PUBLICATIONS

Belitz, "Food Chemistry," 1999, p. 273 [XP002444608].
Boucher et al., "Effect of non-digestible gluco-oligosaccharides on glucose sensitivity in high fat diet fed mice," J. Physiol. Biochem., vol. 59, No. 3, 2003, pp. 169-174 [XP009027711].
International Search Report for PCT/NL2006/050275, dated Aug. 9, 2007, 3 pages.
Weickert et al., "Cereal Fiber Improves Whole-Body Insulin Sensitivity in Overweight and Obese Women," Diabetes Care, vol. 29, No. 4, Apr. 2006, pp. 775-780.

* cited by examiner

*Primary Examiner* — Patrick Lewis
*Assistant Examiner* — Everett White
(74) *Attorney, Agent, or Firm* — Gilberto M. Villacorta; Sunit Palapatra; Foley & Lardner LLP

(57) ABSTRACT

Indigestible oligosaccharides having a molecular weight of 450 Da to 3700 Da are used for the improvement of insulin resistance, the prevention of post-prandial glycaemic dip, and/or the decrease of the post-prandial glucose response of a meal, which is consumed within 72 hours after the consumption of the first product. The oligo-saccharides are especially galacto-oligosaccharides, and are advantageously administered a few hours prior to having the meal.

16 Claims, 2 Drawing Sheets

NUTRITIONAL PRODUCTS COMPRISING SACCHARIDE OLIGOMERS

FIELD OF THE INVENTION

The invention relates to nutritional compositions which comprise oligosaccharides and their clinical use. In particular these oligosaccharides improve the sensitivity of the body to insulin and thus support the effects of insulin.

BACKGROUND

Insulin is a protein that is synthesized by the beta cells of the islets of Langerhans in the mammalian pancreas. Rate of biosynthesis and posttranslational modification are subject to many factors, among which are circulating levels of hormones such as growth hormone and steroids but also due to feeding status. Insulin can be released in the blood as a result of certain triggers, e.g. concentration of glucose and certain amino acids in the blood.

Insulin has a strong effect on energy metabolism in the body. In particular insulin plays an important regulatory role in glucose metabolism, e.g. it activates some glucose transporters, stimulates lipogenesis and diminishes lipolysis, and increases amino acid transport into cells. Energy metabolism depends also on several other factors, such as the level of glucagon or stress hormones in the blood. The concentration of glucagon depends on its turn again on feeding status.

Many subjects suffer from one or more health problems, which can either be solved, alleviated or prevented by interaction with the way a person deals with insulin or by administering insulin itself or compounds that mimic its action. The former method has been predominantly applied in insulin-resistant persons, such as diabetes type II patients, persons suffering from the metabolic syndrome, severely ill persons or persons that experienced severe trauma like surgery or burns, while persons that suffer from severe pancreas damage like patients having diabetes Type I, severe pancreatitis or obstructions of the endocrine function or persons that are malnourished often benefit from the administration of insulin or its analogues.

Because of the high interest of an appropriate action of insulin, many efforts have been made to influence or improve it. Administration of insulin is frequently applied but often occurs parenterally, which is cumbersome to the patient. In addition the effective time period is relatively short, which often makes multiple dosages per day mandatory.

Increase of the sensitivity of mammalian cells to insulin is also frequently aimed for, but is difficult to achieve. Active ingredients like biguanidines are claimed to achieve this.

PRIOR ART

WO 2006/009437 (N. V. Nutricia, 23 Jan. 2006) discloses a nutritional product which improves the sensitivity to insulin or decreases insulin resistance, and contains aspartate equivalents. Such product optionally comprises fiber, preferably wheat bran or low-methylated pectins. However, no effects of the fibers are described.

Weickert et al. disclose in Diabetes Care 2006, 29 (4), 775 that oat fiber, when consumed daily for 3 subsequent days prior to a standard meal, improves whole body insulin sensitivity in overweight and obese women. The oat fiber comprised no oligosaccharides. The product was shown to be ineffective in males or persons with marked insulin resistance such as patients suffering from type II diabetes.

EP 1588629 A1 (N. V. Nutricia, 26 Oct. 2005) discloses a matrix-forming composition comprising low methoxylated pectins and oligosaccharides, more in particular gluco-oligosaccharides (present in Fibersol 2®), the latter promoting the calcium bioavailability throughout the lower gastrointestinal tract. It was shown that both glucose levels, insulin levels and insulin peaks were decreased. The effect of oligosaccharides on the insulin sensitivity per se is not disclosed.

Boucher et al. J. Physiol. Biochem. 59 (3), 169-174 (2003), as well as WO 2004/024167 A2 (Institut National de la Recherche Agronomique, 25 Mar. 2004) from the same authors, disclose the effect of the long-term use of synthetic dietary fiber-like alpha-gluco-oligosaccharides (termed GOS, not to be confused with galacto-oligosaccharide) on the settlement of insulin sensitivity in mice, fed for 20 weeks with a 45% fat diet. It is silent on the short-term insulin sensitivity effect as described in the present application. Galacto-oligosaccharides have not been tested.

EP 1060673 A1 (Nestlé SA, 20 Dec. 2000) discloses a method for selectively increasing the production of proprionate in the gastro-intestinal tract of a mammal, by enterally administering a nutritional composition comprising the polysaccharide dextran to increase the insulin sensitivity. The effect of oligosaccharides, in particular galacto-oligosaccharides is not disclosed.

None of these documents suggest that a single or few dosages of oligosaccharides per se, in particular galacto-oligosaccharides, may be responsible for an increase of insulin sensitivity.

SUMMARY OF THE INVENTION

The present invention allows the manufacture of nutritional products, which possess a high clinical relevance, which are simple to manufacture and convenient to the patient or consumer and are highly palatable.

The products do not need to comprise specific carbohydrate fractions or protein fractions other than disclosed in this document. Due to the optional absence of several ingredients, the products do not need to interfere with normal food consumption.

In addition the products comprising the oligosaccharides according to the invention appear to have an effect which lasts longer than their immediate effect on (a decrease of) plasma concentrations of glucose, in particular during the first two hours after consumption. Even several hours later and even the next day insulin sensitivity can be increased.

The products according to the invention also appear to prevent the occurrence of hypoglycaemia, i.e. periods in which plasma glucose concentration is below 4 mM and affect the post-prandial glucose response which results from the consumption of a different nutritional product, consumed after the product according to the invention.

DETAILED DESCRIPTION OF THE INVENTION

Figure 1:
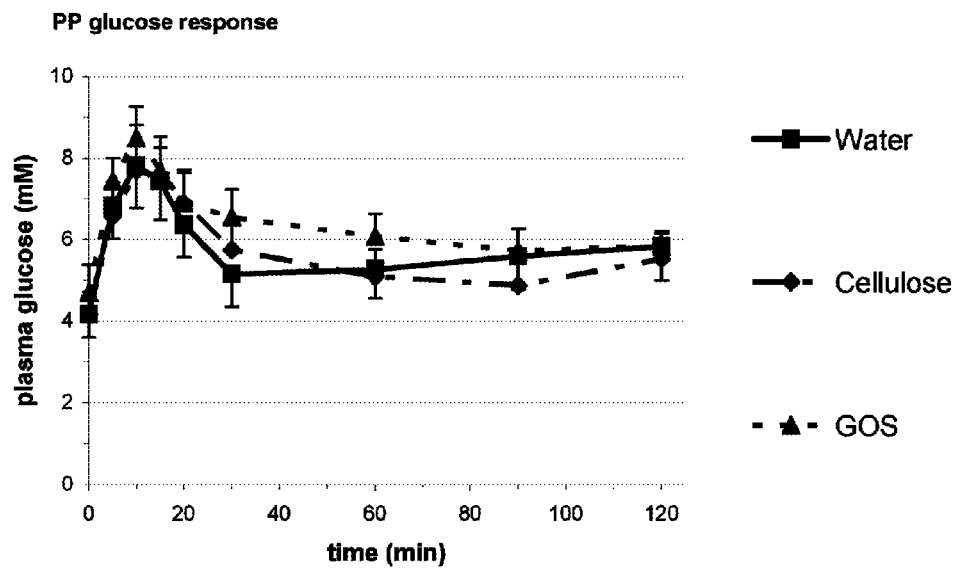
FIG. 1 depicts the postprandial glucose response upon maltodextrin injection 24 h in rats after pretreatment with water, cellulose, and galacto-oligosaccharides, respectively.

It has been found that oligosaccharides can be used in the manufacture of nutritional or pharmaceutical compositions that are effective in the prevention of a glycaemic dip and/or the increase of insulin sensitivity and/or the decrease of the post-prandial glucose response (abbreviated as PPGR), as observed after consumption of a subsequent nutritional product.

In a first embodiment, the invention relates to the use of indigestible oligosaccharides having a molecular weight of 450 Da to 3700 Da in the manufacture of a nutritional or pharmaceutical product for the improvement of insulin resistance, the prevention of post-prandial glycaemic dip, and/or the decrease of the post-prandial glucose response of a meal, which is consumed within 72 hours after the consumption of said product.

In the context of this application, the "Da" is an abbreviation for dalton. It is a non-SI unit of mass, equal to the unified atomic mass unit (atomic mass constant, uamu) and is equal to about $1.66054 \times 10^{-27}$ kg.

In the context of this application, meal is any consumption of food, giving rise to a glucose response. This may include complete and supplemental foods, medicinal food products, snacks, drinks, etc., in particular for children, adolescents and elderly, both man and women.

The term 'glycaemic dip' is used herein to denote a decrease of the plasma glucose level after a meal until below the level prior to taking the meal. Such a dip can occur between one and several hours after a meal, in particular after about 2 hours. Usually, the glucose level will rise again after e.g. half an hour to about 5 hours. Such a glycaemic dip may occur both in persons suffering from diabetic conditions, i.e. a person having a hampered insulin management, and in persons not suffering from such diabetic conditions. In non-diabetic persons, the glycaemic dip can result in craving behaviour and frequent eating events ("binge eating") or to feelings of fatigue and weakness. In diabetic patients, the glycaemic dip can lead to even more serious effects as described below, and is usually referred to as hypoglycaemia. The invention is concerned with both forms of a glycaemic dip.

The effect on glycaemic dips, including hypoglycaemia, can be measured by either determining the plasma glucose concentrations (PG) after consumption or administration of the nutritional product itself or by determining PG after consumption of a second, third or other sequential nutritional product that is consumed at least 30 minutes up to 72 hours after consumption of the product according to the invention.

Periods of hypoglycaemia are defined as being those time periods in which the concentration of glucose in plasma decreases to a value below 4 mM, when measured within 5 hours after consumption of the product according to the invention or of a sequential meal that is consumed within 72 hours after the administration of the product according to the invention.

Indicative of the likelihood that a period of hypoglycaemia can occur is the period in which plasma glucose concentration is below the baseline value after administration of a bolus feeding of a product having a predetermined amount of carbohydrates to a fasted subject. If PG is plotted against time, the PG typically reaches a peak value after 30 to 90 minutes and will subsequently start to decrease rapidly to the baseline value (PG at time of administration), which will occur after 2 to 3 hours. Normally, the metabolic reaction of healthy consuming persons will prevent that PG will become too low. Diabetics and insulin resistant persons however have difficulties in maintaining glucose homeostasis.

Periods of hypoglycaemia result in craving behaviour and frequent eating events or, when no food is taken at appropriate times, to feelings of fatigue and weakness, dizziness and even fainting or in extreme situations even coma or death. The problem of hypoglycaemia is particularly important during night time and for infants, in particular for those infants who do not yet have adequate experience with their pathology.

The effect of the product on the decrease of insulin resistance (or increase of insulin sensitivity) can be determined by the reference insulin clamp technique as known in the art or by assessing the Matsuda index, which is more convenient to apply. In the latter case the product is given to a person and subsequently the concentrations of glucose and insulin in blood plasma are determined. The ratio of insulin to glucose is a measure of the sensitivity of the body to the amount of insulin that is released.

Such improvement of insulin sensitivity appears to be longer lasting. It will last for at least 3 days. For example the effect of the nutritional or pharmaceutical product of the invention has become evident by determining the postprandial glucose response after consumption of a second or other subsequent meal, which had been consumed within 72 hours after consumption of the first product.

Hence, the oligosaccharides to be used according to the invention can surprisingly serve both to reduce the postprandial high glucose levels (hyperglycaemia), as well as reduce or prevent the glycaemic dip (hypoglycaemia), which can occur subsequently, or independent from a hyperglycaemic event. The oligosaccharides exert these functions especially when administered prior to a meal up to 72 hours, in particular up to 48 hours, in particular up to 24 hours, in particular up to 12 hours, in particular up to 5 hours, in particular between 30 minutes and 5 hours prior to the meal, in particular between 1 hour and 5 hours prior to the meal, in particular between 2 hours and 5 hours prior to the meal, in particular between 3 hour and 5 hours prior to the meal.

It has been found that this property of the oligosaccharides alone enables the user to maximize the health beneficial properties of other components that are present in the food or of active ingredients and allow the manufacture of new products that are better suited for meeting the demands of insulin-resistant persons and diabetics.

Such products include products providing less than 250 kcal (1050 kJ), preferably 20 to 200 kcal (84 to 840 kJ) and more preferably 50 to 180 kcal (210 to 756 kJ) per serving unit. Such serving unit is preferably ready for use and includes products having a solid, semi-solid or liquid form. Examples of a solid product are a bar, cake or sweetie. Examples of a semi-solid product are a snack, pudding or porridge. Examples of liquids are drinks having a volume equal to or less than 200 ml. These serving units thus provide an energy density of preferably equal to or less than 1.25 kcal/ml (5.25 kJ/ml), preferably from 0.1 to 1 kcal/ml (0.42 to 4.2 kJ/ml), more preferably from 0.25 to 1 kcal/ml (1.05 to 4.2 kJ/ml), and even more preferably from 0.25 to 0.9 kcal/ml (1.05 to 3.78 kJ/ml), very particularly 0.3-0.9 kcal/ml (1.26-3.78 kJ/ml). However, smaller volumes may have a higher energy density, such as equal to or less than 2.50 kcal/ml (for a 100 ml serving unit), and equal to or less than 5.0 kcal/ml (for a 50 ml serving unit).

The products according to the invention should comprise indigestible oligosaccharides (OS). Such OS are defined to be those molecules that comprise more than 93 weight percent (wt %) saccharide moieties, and having a molecular weight of 450 Da to 3700 Da in the form attained when dissolved in pure water of neutral pH (degree of polymerization of 3-20). Preferably, the molar weight of the OS may range between 450 Da and 3300 Da, most preferably between 450 Da and 1700 Da, or even up to 1000 Da.

The presence of indigestible saccharides having a higher molar weight is not detrimental. However, it is preferred that the majority of molecules, in number, but preferably also in weight, has the molar weight as indicated for the indigestible OS. For example, it is preferred that less than 50% has a molar weight over 3700 Da, especially less than 50% over 3300 Da. The desirability of the presence of molecules having a lower molar weight than 450 (essentially disaccharides) depends on the nature of the OS, and on the specific needs of the patients. In case of galacto-oligosaccharides, the lower MW molecules (disaccharides) may include galactosylgalactose and lactose. The former is believed to have the same function as the higher MW molecules, while the presence of the digestible is usually beneficial, except for lactose-resistant patients. In case of pectin hydrolysates as another example, the majority of disaccharides will be indigestible and contain galacturonic acid units, and be acceptable or even beneficial.

The oligosaccharide molecules can be linear or branched and can have the saccharide moieties attached to each other via alpha-1,2, alpha-1,3, alpha-1,6 and beta-1,1, beta-1,2, beta-1,3, beta-1,4 and beta-1,6 or mixtures thereof, but cannot be attacked by the amylases present in the human digestive tract or by the brush border saccharidases present in the epithelial cells and are therefore not digested, nor are digestion products available for absorption into the plasma compartment.

Preferably, the oligosaccharide molecules according to the invention comprise more than 50 wt %, more preferably more than 60 wt %, especially more than 70 wt % of units selected from the group of galactose units, xylose units, arabinose units, and mixtures thereof. Optionally, at least 10 wt % of the remainder of the saccharide units in the oligosaccharide molecules may be different, and may be selected from the group of glucose units, rhamnose units, fucose units, mannose units, and mixtures thereof. A part or even all of the saccharide units may be derivatised, e.g. as uronic acids and/or acylates.

However, best results with regard to efficacy are obtained by using the OS which comprise more than 60 wt % of galactose units, even more preferably from 70 to 100 wt % of galactose units, and most preferably from 73 to 90 wt % of galactose units. The remainder of the saccharide units are preferably for more than 10 wt % glucose units.

Preferably, the galactose units in the OS are attached to each other for more than 70% via beta bonds. Such galacto-oligosaccharides can be prepared by adding galactose to a guest molecule, by means of adding appropriate enzymes as known in the art. Such guest molecule can be lactose or other molecules as occur in soy. Suitable galacto-oligosaccharides can be obtained by transgalactosylation of lactose by β-galactosidase. Other examples of suitable oligosaccharides include hydrolysed arabinogalactans, hydrolysed arabinans and hydrolysed arabinoxylans, for example as described in WO 02/051264.

The oligosaccharides can be part of a non-digestible or nutritional fiber fraction. The total amount of this non-digestible fraction or fiber fraction is determined by applying the method as known in the art for the matrix involved, e.g. the AOAC method for determining "Total Dietary Fiber", and the method of McCleary for determining resistant starch amount and for measurement of the amounts of OS or polyol compounds chromatographic methods and appropriate summation of these amounts, or alternatively, by judgment of the label for those food components that have to be declared as nutritional fiber.

The weight of the OS should contribute at least 20 wt %, especially at least 30 wt %, preferably from 36 wt %, up to 100 wt %, in particular at least 44 wt %, and most preferably equal to or more than 50 wt % to the weight of the non-digestible (i.e. fiber) fraction in the product.

Preferably, the OS are galacto-oligosaccharides which provide more than 36 wt %, preferably more than 44 wt %, more preferably more than 51 wt %, more preferably more than 70 wt % and most preferably more than 90 wt % of the total weight of the non-digestible fraction in the product in order to obtain maximum effect on insulin resistance, PPGR of a sequential meal and the decrease of the frequency of the prevalence or a decrease of the degree of hypoglycaemia in patients suffering from insulin resistance.

The fiber fraction in the products can comprise alternative fibers, such as other OS having a degree of polymerization of 3-20, including arabino-oligosaccharides, xylo-oligosaccharides, uronic acid oligomers, resistant dextrin, resistant starch, gums, and insoluble fibers. It is preferred to include a variety of fibers in terms of fermentation pattern and molecular structure, for achieving additional benefits, such as support of the gut function and behaviour, support of immune function, decrease sensitivity to allergens or an improvement of the digestive processes.

Though the inclusion of resistant starch can be very beneficial it has been found that in liquid products it is better to restrict the amount of resistant starch in liquid products to less than 64 wt %, preferably less than 50 wt %, and more preferably less than 30 wt % of the fiber fraction in order to improve palatability.

In case uronic acid oligomers are included, an improvement of the immune system may be obtained. This is achieved best by using uronic acids which are protected for only a small part by alkylation. When pectin is used as source of uronic acids, in particular a non-methoxylated or a pectin which is methoxylated to a low degree only (e.g. less than 25%, especially less than 10%) should preferably be used as the source. The use of uronic acid oligomers instead of pectins avoids solidification of the liquid product both in the package and in the digestive tract (e.g. in the stomach when calcium salts are dissolved) and does not impart digestion processes in the stomach, even when soluble or insoluble calcium is included in the product and in this way prevents the occurrence of hypoglycaemia in diabetics who need food, in particular when they already have administered insulin to themselves. Such low methoxylated pectins are known in the art. Such product preferably comprises uronic acid sources in the form of OS having a degree of polymerization of 2-20.

The use of pectin per se (as polysaccharide, with a DP>20), and in particular the use of low-methoxylated pectins should best be avoided, as these tend to form a solid matrix in the stomach, leading to gastroparesis, which is undesirable in diabetic patients for the reasons mentioned above. In general, the use of matrix forming fibers should be avoided to the extent a matrix is formed in the stomach and e.g. providing a sense of satiety.

Hence the invention relates to the use of indigestible oligosaccharides having a molecular weight of 450 Da to 3700 Da in the manufacture of a nutritional or pharmaceutical product for the improvement of insulin resistance, the prevention of post-prandial glycaemic dip, and/or the decrease of the post-prandial glucose response of a meal, which is consumed within 72 hours after the consumption of said product, in the absence of matrix-forming fibers, in particular in the absence of (non-hydrolysed) pectin, more in particular in the absence of low-methoxylated pectin. With "in the absence of" is meant that essentially no or only to a low extent these pectins are present in the stomach, leading to matrix-forming, gastroparesis and/or hypoglycaemia.

The amount of nutritional fiber that should be consumed in order to be effective is at least 3 g per serving unit, preferably from 4 to 40 g per serving unit, more preferably from 5 to 20 g per serving unit. The amount of indigestible OS of the invention can be administered in an amount of 1 to 30 g per serving unit, preferably 2 to 20 g per serving unit, most preferably 3 to 12 g per serving unit.

Preferably, such serving unit is to provide maximally 250 kcal (1050 kJ), thus leading to a nutritional fiber amount of at least 1.2 g/100 kcal (0.29 g/100 kJ), preferably from 1.7 g/100 kcal to 419 g/100 kcal (0.4 g/100 kJ to 100 g/100 kJ), more preferably from 2.1 g/100 kcal to 335 g/100 kcal (0.48 g/100 kJ to 80 g/100 kJ), and most preferably from 2.0 g/100 kcal to 251 g/100 kcal (0.6 g/100 kJ to 60 g/100 kJ).

The amount of indigestible oligosaccharides in said nutritional fibres is preferably at least 0.24 g/100 kcal (0.06 g/100 kJ), more preferably at least 0.36 g/100 kcal (0.09 g/100 kJ), more preferably at least 0.60 g/100 kcal (0.14 g/100 kJ), and in particular at least 1.18 g/100 kcal (0.28 g/100 kJ), up to 80 g/100 kcal (19 g/100 kJ, preferably up to 25 g per 100 kcal (6 g/100 kJ). more preferably up to 16.8 g/100 kcal (4 g/100 kJ). Preferred ranges are thus from 0.36 g/100 kcal to 80 g/100 kcal (0.09 g/100 kJ to 19 g/100 kJ), and most preferably from 0.60 g/100 kcal to 25 g/100 kcal (0.14 g/100 kJ to 6 g/100 kJ).

The energy-providing components of the products may be digestible carbohydrates, protein and lipids. It is preferred that the product contains at least digestible carbohydrates or proteins, or both. Therefore, in this application, energy amounts are calculated based on the energy provided by the digestible carbohydrate and, if present, protein and lipid fraction.

The amount of fibre is typically at least 15 wt % with respect to the weight of the digestible carbohydrate fraction, preferably from 20 to 400 wt %, more preferably from 30 to 200 wt % of the digestible carbohydrates. The amount of indigestible oligosaccharides as defined above is preferably at least 8 wt %, preferably from 15 to 150 wt %, and most preferably from 25 to 125 wt % of the digestible carbohydrates.

Hence, a typical composition according to the invention containing 100 kcal (418 kJ), may comprise:
  0 to 13 g, preferably 1 to 11 g, more preferably 1 to 10 g, and most preferably 3 to 9 g of digestible carbohydrates;
  0 to 22.5 g, preferably 2 to 20 g, and most preferably 4 to 17.5 g of protein, the total of protein and digestible carbohydrates being at least 15 g; and
  0 to 5 g, preferably 0.1 to 4 g of lipids.

However, in special cases, the energy content may be exclusively provided by either digestible carbohydrates, or proteins. In addition, the composition of 100 kcal contains oligosaccharides, preferably from 2.5 to 25 g. The unit dosage may be these 100 kcal, but lower and higher amounts, e.g. 50 kcal, 75 kcal, 125 kcal, 150 kcal or 200 kcal are also well suited. As already mentioned, the unit dosage, as one serving unit, preferably should not exceed 250 kcal per serving.

The oligosaccharides of the invention are beneficially included in food products that comprise a digestible carbohydrate fraction. Though consumption of rapidly available carbohydrates was suspected to contribute to the obesity problem, the inventors believe that the amount of rapidly available carbohydrates in this product should preferably be more than 45 wt % of the digestible carbohydrate fraction in the product.

Examples of such rapidly available and easily digestible carbohydrates are glucose or its precursors, such as glucose polymers selected from the group of glucose syrup, maltodextrins and easily digestible starches, as well as sucrose and lactose and galactose. Preferably, lactose contributes at least 2 wt %, preferably from 4 to 80 wt %, and most preferably from 8 to 65 wt % of the digestible carbohydrate fraction.

Furthermore, it is also advantageous to include slowly available carbohydrates as palatinose (isomaltulose), being a low glycaemic carbohydrate leading not only to a low glycaemic response but as well to a prolonged glucose supply. Preferably, palatinose contributes at least 2 wt %, preferably from 4 to 80 wt %, and most preferably from 8 to 65 wt % of the digestible carbohydrate fraction.

Preferably, the total amount of digestible carbohydrates is advantageously less than 50 energy percent (En %, kJ per 100 kJ), preferably less than 44%, more preferably from 4 to 40 En %, and most preferably from 12 to 36 En %. The contribution to the energy content of a product is known in the art, using the Atwater constants for digestible carbohydrates, lipids and proteins and attributing nil energy to fibers or other food constituents, while following the regulations for labelling practices.

The oligosaccharides according to the invention are beneficially included in food products that comprise a protein fraction. Suitable proteins are those which are commonly accepted in food products. In a preferred embodiment, the protein fraction represents 0 to 90 En %, more preferably 20 to 80 En %, and most preferably 40 to 70 En %, relative to the energy content of the product as provided by proteins, digestible carbohydrates and lipids.

The nature and concentration of other food constituents which can be included, such as lipids and micro ingredients, can be selected by the skilled person, on the basis of the specific needs of the intended users. A lipid fraction, if present, represents between 1 and 40 En %, preferably between 10 and 30 En % of the product, especially less than 24 En %.

In one embodiment, the invention relates also to a nutritional composition comprising a fiber fraction and a digestible carbohydrate fraction, and a protein and/or lipid fraction, wherein the fiber fraction comprises more than 36 wt % of oligosaccharides having a molecular weight of 450 Da to 3700 Da and comprising more than 60 wt % of galactose units, and wherein the oligosaccharides are included in an amount of 0.24 g/100 kcal to 16.8 g/100 kcal (0.06 g/100 kJ to 40 g/100 kJ) as provided by the digestible carbohydrate and, if present, protein and lipid fraction, and wherein the amount of digestible carbohydrates is less than 50 kJ per 100 kJ (50 En %)

Furthermore, the OS according to the invention can also be beneficially included in pharmaceutical products, comprising one or more active ingredients. In this way the effect of the active ingredient is supported, which ensures that less active ingredient is required, which decreases the amount of side effects. In addition, the OS according to the invention provide an excellent vehicle or excipient which stabilizes the active ingredient.

In particular, powders can be compiled that comprise the OS according to the invention and active ingredients that are effective in the treatment of diabetes, such as insulin, DPP-IV inhibitors, thiazolidinediones or PPAR-gamma agonists, sulfonylurea compounds, meglitinides and biguanidines, statins, and acetylcholine esterase inhibitors. An example of a suitable biguanidine compound is metformin, of thiazolidinedione compounds pioglitazone, troglitazone and rosiglitazone, of a meglitimide compound repaglimide and nateglimide of sulfonylurea compounds tolbutamide, tolazamide, glipizide, gliclazide, glimepizide, glibenclamide and glybuzide and of DPP-IV inhibitors are saxaglyptin, sitaglyptin and vildagliptin. Examples of suitable statins are atorvastatin, cerivastatin, fluvastatin, lovastatin, mevastatin, pitavastatin, pravastatin, rosuvastatin and simvastatin. Examples of suitable cholinesterase inhibitors are the reversible inhibitors. These include carbamate derivatives such as physostigmine, neo-stigmine, pyridostigmine, rivastigmine, ambenonium and demarcarium, phenanthrene derivatives like galantamide, piperidines like donepezil and several organophosphate compounds like metrifonate. Preferably, the active ingredient is selected from the group of insulin, biguanidines, statins, and acetylcholine esterase inhibitors.

Such active ingredients can be included into the formula in lower concentrations than when administered as single active component and still cause a beneficial effect. In particular, the dosage can typically be more than 40% less while still providing the same beneficial effect. This will decrease the side effects, which are known in the art, including the decrease in efficacy during long term use. Typical dosages vary from one active ingredient to another, however the dosages will typically be in the range of 0.01 to 20 mg per serving unit, except for insulin.

Such powders are suitably dissolved in a liquid. However, the levels of protein, lipids and digestible carbohydrates will be that low that the amount of energy in the solution that is administered is below 19 kcal/100 ml (80 kJ/100 ml). Accordingly, the invention relates to such dry formulation or solution. In particular, it relates to a dry formulation comprising a fiber fraction and a digestible carbohydrate fraction, and a protein and/or lipid fraction, wherein the fiber fraction comprises more than 36 wt % of oligosaccharides having a molecular weight of 450 Da to 3700 Da and comprising more than 60 wt % of galactose units, and wherein the oligosaccharides are included in an amount of 0.24 g/100 kcal to 16.8 g/100 kcal (0.06 g/100 kJ to 40 g/100 kJ) as provided by the digestible carbohydrate and, if present, protein and lipid fraction, and wherein the amount of digestible carbohydrates is less than 50 kJ per 100 kJ (50 En %).

The OS, or the product containing these, can be administered prior to a regular meal, at the dosage levels indicated above. The OS can be administered between 30 minutes and 5 hours, preferably between 1 hour and 3 hours prior to an individual meal. The OS can be administered between once and several times per day, preferably at least prior to the main meal. Surprisingly, it was found that the OS also have a long-term effect, up to 48, or even up to 72 hours prior to the individual meal. Hence, the OS can also be administered once, for an isolated preventive intervention on hypoglycaemia, or once per 2 or 3 days. The invention further relates to embodiments where the OS are given either as a separate and distinct administration prior to the meal, or as part of a complete meal. Hence, when the OS are administered as part of a as a complete meal, the invention also relates to the repetitive and sequential administration of the same complete meal, within a period of 72 hours.

EXAMPLES

Example 1

Nutritional Bar Suitable for Use as a Night Time Formula for Reducing the Glycaemic Dip in Diabetic Children A bar for infants weighing about 25 g was produced from:
about 8.5 g protein (milk protein and soy protein) (34 kcal)
about 4 g cut dried raisin/apricot blend providing about 2.0 g digestible carbohydrates (8 kcal)
about 4 g glucose syrup (16 kcal)
about 1 g lipids comprising about 50 mg docosahexaenoic acid (9 kcal)
about 4 g galacto-oligosaccharides (the ingredient providing about 1.5 g lactose) (6 kcal lactose)
about 1 g vitamins/minerals blend providing at least biotin, vitamin B6, vitamin B12 and zinc The mass balance is made up with moisture/water in the bar.

Example 2

Product Suitable for Use as a Product Before Having Dinner

Amuse, prepared by blending per 1000 kg:
about 300 kg mixed protein source (milk protein and meat powder), including about 87 wt % protein, about 8 wt % lipids, and about 3 wt % carbohydrates; the remainder being ash
about 100 kg milled dry pea (providing about 20 wt % protein, about 80 wt % digestible carbohydrates)
about 80 kg galacto-oligosaccharides, including about 10 kg lactose
about 10 kg low methoxylated pectin hydrolysate
about 50 kg lipids (including lecithins)
about 80 kg dextrins
about 30 kg texturisers
about 50 kg salts, herbs and flavourings
about 1 kg vitamin/mineral blend
about 1 kg antioxidants and colorants The remainder is water to make up to 1000 kg.

After dissolving the dry ingredients, a paste is prepared which is packaged in appropriate unit sizes of 10-500 g.

Example 3

Product Suitable for Use as a Sip Feed for Diabetics

Energy: 87 kcal/100 ml (360 kJ/100 ml)
The product comprises per 100 ml:
Protein about 6 g (milk protein and pea protein) (24 kcal)
Lipids about 3 g (20 marine oil/40 rape seed/20 corn/20 MCT) (27 kcal)
Digestible carbohydrates about 9 g (about 15 wt % lactose/ about 85 wt % glucose oligomers) (36 kcal)
Fiber 2 g (about 60 wt % galacto-, arabinose- or xylose-oligomers, about 40 wt % resistant starch)
Micro-ingredients (minerals, vitamins, trace elements, flavourings, colorants, etc.)

Example 4

Second More Energy-Rich Product Suitable as a Sip Feed for Diabetes

Energy: 100 kcal/100 ml (420 kJ/100 ml)
The product comprises per 100 ml:
Protein about 4.9 g (alpha-lactalbumin enriched whey and soy protein) (20 kcal)
Lipids about 3.8 g (mixture of rape seed, sunflower and fish oil) (34 kcal)
Digestible carbohydrates about 11.7 g (about 30 wt % lactose/about 38 wt % palatinose/about 27 wt % clear-gum/about 5% of glucose, etc.) (46 kcal)
Fiber about 2 g (about 50 wt % galacto-oligomers, mixture of cellulose, resistant dextrine and resistant starch)

Micro-ingredients (minerals, vitamins, trace elements, flavourings, colorants, etc.)

Example 5

Third More Energy-Rich Product Suitable as a Sip Feed for Diabetes

Energy: 100 kcal/100 ml (420 kJ/100 ml)
The product comprises per 100 ml:
Protein about 4.9 g (alpha-lactalbumin enriched whey and soy protein) (20 kcal)
Lipids about 3.8 g (mixture of rape seed, sunflower and fish oil) (34 kcal)
Digestible carbohydrates about 11.6 g (about 13 wt % lactose/about 87 wt % of a mixture of palatinose, cleargum and glucose) (46 kcal)
Fiber about 2 g (about 50 wt % galacto-oligomers, mixture of cellulose, resistant dextrine and resistant starch)
Micro-ingredients (minerals, vitamins, trace elements, flavorants, colorants, etc.)

Example 6

Product Suitable for Use in the Morning to Decrease Morning Hyperglycaemia in Diabetics Energy: 60 kcal/100 ml (250 kJ/100 ml)
The product comprises per 100 ml:
Protein about 10 g (milk protein) (40 kcal)
Digestible carbohydrates about 5 g (about 15 wt % lactose/about 85 wt % glucose oligomers) (20 kcal)
Fiber about 10 g (about 60 wt % galacto-oligomers, about 20 wt % pectin, about 20 wt % resistant starch)
Micro-ingredients (minerals, vitamins, trace elements, flavorants, colorants, etc.)

EXPERIMENTAL

In animal experiments employing healthy adult male Wistar rats (n=7) an improvement in the insulin sensitivity was observed as a 'second day effect' of administered galacto-OS fiber (GOS).

Animals were given the galacto-OS fiber (GOS) load via a gastric canula on day 1. A 6 ml bolus load was administered equal to 50% of their daily fiber intake; fiber was dissolved in water. About 24 hours later (on day 2) an oral glucose tolerance test was carried out and the postprandial glucose and insulin course was monitored for 120 min upon the intragastric injection of a carbohydrate load (2 g maltodextrin/kg BW). To this end blood samples were drawn repeatedly via a jugular vein canula.

Intragastric injection of water or a cellulose solution in water on day 1 served as control. As the GOS fiber preparation consisted of 50% of digestible carbohydrates, the two control injections were co-administration with carbohydrates to correct for this.

Figure 2:
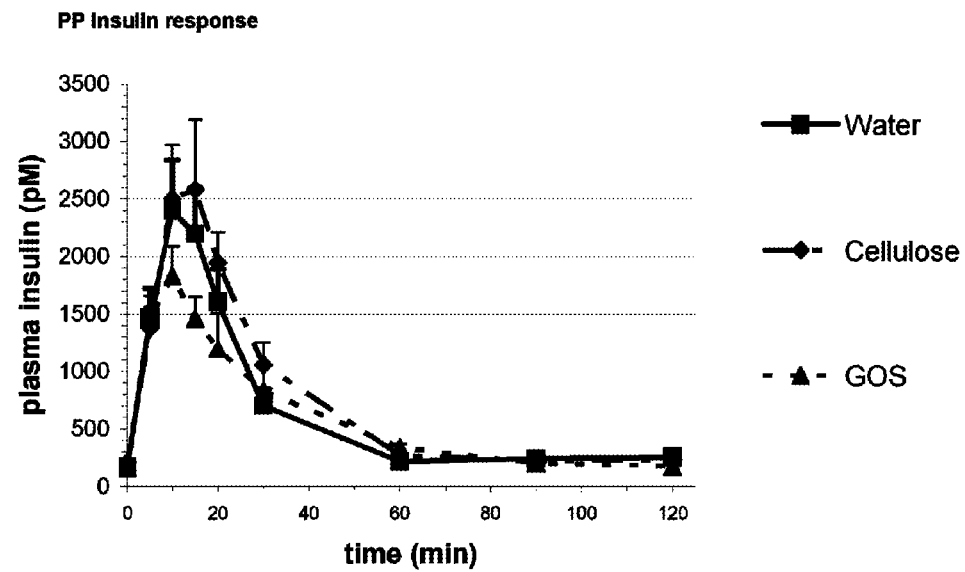
FIG. 2 depicts the postprandial insulin response upon maltodextrin injection 24 h in rats after pretreatment with water, cellulose, and gal acto-oligosaccharides, respectively.

FIGS. 1 and 2 depict the postprandial course of glucose and insulin plasma levels, respectively, for each of the three pre-treatments.

Figure 3:
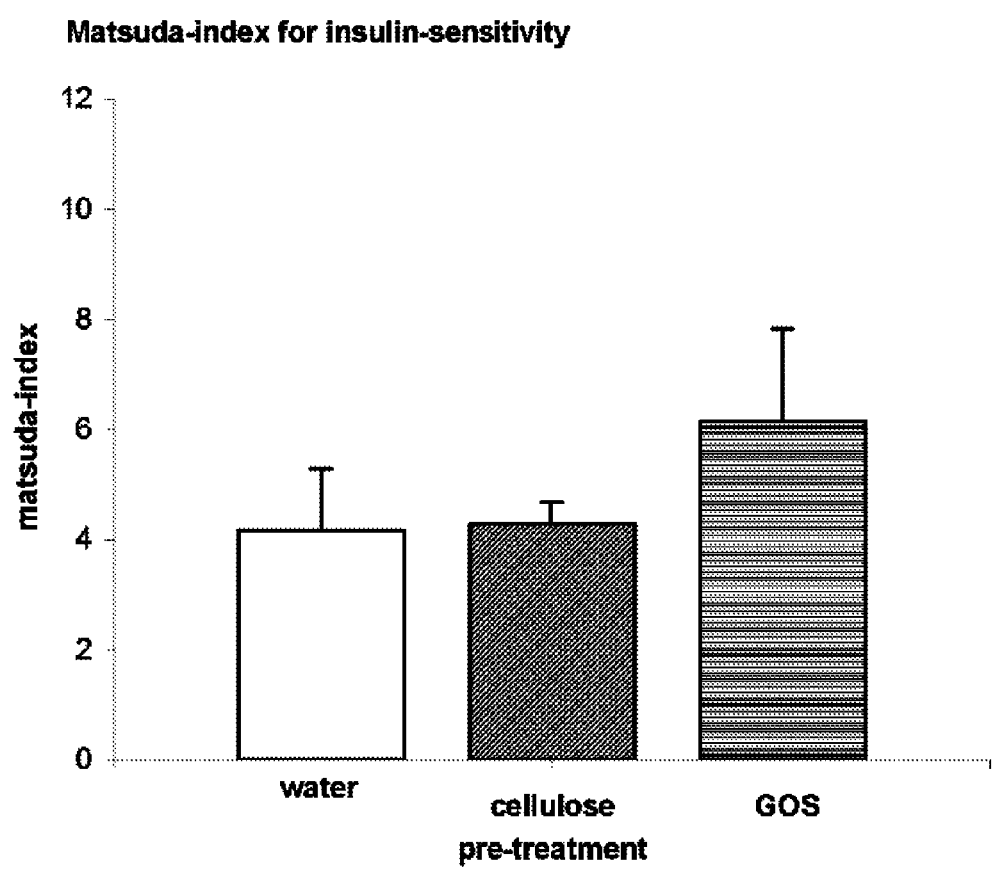
FIG. 3 depicts the Matsuda index for insulin sensitivity after pretreatment with water, cellulose, and galacto-oligosaccharides, respectively.

The postprandial plasma glucose excursions do not differ between the three pre-treatments (FIG. 1). In contrast, pre-treatment with galacto-OS fibers (GOS) clearly decreases the amount of insulin secreted (FIG. 2), resulting in significant (p<0.05) lower incremental AUC values. The calculated Matsuda-index, an index for insulin sensitivity, is hence increased upon pre-treatment with galacto-OS (FIG. 3).

The invention claimed is:

1. A method for improvement of insulin resistance, prevention of post-prandial glycaemic dip, and/or for decreasing post-prandial glycaemic response in a subject following consumption of a meal, the method comprising administering to the subject a composition comprising an effective amount of indigestible oligosaccharides having a molecular weight of 450-3700 Da, and comprising:
    (a) more than 60 wt % galactose units and
    (b) more than 10 wt % of monomer units selected from glucose units, mannose units and mixtures thereof,
    wherein the meal is consumed within 72 hours after administration of the composition.

2. The method according to claim 1, wherein the oligosaccharides comprise from 73 to 90 wt % of galactose monomer units, and wherein more than 10 wt % of the remainder of saccharide monomer units are glucose units.

3. The method according to claim 1, wherein the indigestible oligosaccharides are administered in an amount of 2 to 20 g per serving unit.

4. The method according to claim 1, wherein the composition further comprises at least 1.2 g/100 kcal (0.29 g/100 kJ) of nutritional fiber.

5. The method according to claim 1, wherein the composition further comprises lipids and proteins.

6. The method according to claim 1, further comprising digestible carbohydrates, which provide less than 50 En % in the composition and comprise more than 45 wt % of digestible glucose sources selected from the group consisting of glucose, glucose syrup, maltodextrins and digestible starch.

7. The method according to claim 1, wherein the oligosaccharides are used in the absence of pectin.

8. The method according to claim 1, wherein the meal is consumed within 24 hours after administration of the composition.

9. The method according to claim 8, wherein the meal is consumed within 12 hours after administration of the composition.

10. The method according to claim 9, wherein the meal is consumed between 1 and 5 hours after administration of the composition.

11. A nutritional composition comprising:
    (a) a fiber fraction comprising more than 36 wt % of oligosaccharides having a molecular weight of 450 Da to 3700 Da and comprising (i) more than 60 wt % of galactose units and (ii) more than 10 wt % of units selected from glucose units, mannose units and mixtures thereof, wherein the oligosaccharides are present in an amount of 0.24 g/100 kcal to 16.8 g/100 kcal (0.06 g/100 kJ to 4.0 g/100 kJ);
    (b) less than 50 kJ per 100 kJ (50 En %) of a digestible carbohydrate fraction; and
    (c) a protein fraction in an amount between 20 and 80 kJ per 100 kJ.

12. The nutritional composition of claim 11, further comprising a lipid fraction.

13. The composition according to claim 12, wherein the amount of digestible carbohydrates is between 4 and 50 kJ, and the amount of lipids is less than 24 kJ per 100 kJ.

14. A nutritional composition comprising:
    (a) a fiber fraction comprising more than 36 wt % of oligosaccharides having a molecular weight of 450 Da to 3700 Da and more than 60 wt % of galactose units, wherein the oligosaccharides are present in an amount of 0.24 g/100 kcal to 16.8 g/100 kcal (0.06 g/100 kJ to 4.0 g/100 kJ);

(b) less than 50 kJ per 100 kJ (50 En %) of a digestible carbohydrate fraction;
(c) a protein fraction in an amount between 20 and 80 kJ per 100 kJ; and
(d) one or more active ingredients selected from the group consisting of insulin, biguanidines, statins, and acetylcholine esterase inhibitors.

15. The method according to claim 3, wherein the serving unit provides 20 to 200 kcal (84 to 840 kJ).

16. The method according to claim 3, wherein the serving unit provides 50 to 180 kcal (210 to 756 kJ).

* * * * *

UNITED STATES PATENT AND TRADEMARK OFFICE
CERTIFICATE OF CORRECTION

PATENT NO. : 8,637,487 B2 Page 1 of 1
APPLICATION NO. : 12/513330
DATED : January 28, 2014
INVENTOR(S) : Van De Heijning et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 886 days.

Signed and Sealed this
Twenty-second Day of September, 2015

Michelle K. Lee
*Director of the United States Patent and Trademark Office*